(12) United States Patent
Thum et al.

(10) Patent No.: US 8,404,470 B2
(45) Date of Patent: Mar. 26, 2013

(54) ENZYME PREPARATIONS FOR USE AS BIOCATALYSTS

(75) Inventors: Oliver Thum, Ratingen (DE); Marion Ansorge-Schumacher, Roetgen (DE); Lars Wiemann, Berlin (DE); Andreas Buthe, Grenzach-Wyhlen (DE)

(73) Assignee: Evonik Goldschmidt GmbH, Essen (DE)

( * ) Notice: Subject to any disclaimer, the term of this patent is extended or adjusted under 35 U.S.C. 154(b) by 1260 days.

(21) Appl. No.: 12/168,350

(22) Filed: Jul. 7, 2008

(65) Prior Publication Data
US 2009/0017519 A1 Jan. 15, 2009

(30) Foreign Application Priority Data

Jul. 6, 2007 (DE) .......................... 10 2007 031 689

(51) Int. Cl.
*C12N 11/08* (2006.01)
(52) U.S. Cl. .................... 435/180; 435/177; 106/287.13
(58) Field of Classification Search .......................... None
See application file for complete search history.

(56) References Cited

U.S. PATENT DOCUMENTS 5,494,815 A 2/1996 Von Gentzkow et al.

FOREIGN PATENT DOCUMENTS

| EP | 0 231 093 A | 8/1987 |
| EP | 0 562 371 A | 9/1993 |
| WO | WO 03/106607 | 12/2003 |

OTHER PUBLICATIONS

Guo et al (2008 J. Applied Polymer Science 108:1901-1907).*
Wiemann et al (2009 ChemCatChem 1:455-462).*
Hoyos P. et al., Journal of Molecular Catalysis B: Enzymatic, vol. 52-53, Jun. 1, 2008, pp. 133-139, ISSN: 1381-1177.
Buthe et al., Journal of Molecular Catalysis B: Enzymatic, vol. 35 4-6, Sep. 1, 2005, pp. 93-99, ISSN: 1381-1177.
Bruno et al., World Journal of Microbiology & Biotechnology 2005 21, Mar. 1, 2005, pp. 189-192, ISSN: 1573-0972.

* cited by examiner

*Primary Examiner* — Christopher M Gross
(74) *Attorney, Agent, or Firm* — Frommer Lawrence & Haug LLP

(57) ABSTRACT

The invention is directed to enzyme preparations which are obtainable by enzyme immobilizates which comprise enzymes or microorganisms containing enzymes immobilized on an inert carrier being provided with a silicone coating obtained by hydrosilylation, to a process for producing such enzyme preparations and to the use of enzyme preparations as an industrial biocatalyst.

12 Claims, 1 Drawing Sheet

ENZYME PREPARATIONS FOR USE AS BIOCATALYSTS

This application claims benefit under 35 U.S.C. 119(a) of German patent application DE 10 2007 031 689.7, filed on 6 Jul. 2007.

Any foregoing applications including German patent application DE 10 2007 031 689.7, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

The invention relates to novel enzyme preparations for use as biocatalysts.

Microorganisms and isolated enzymes find wide use as a catalyst in the chemical industry or in food production. An overview is offered, for example, by: A. Liese, K. Seelbach, C. Wandrey, Industrial Biotransformations, Wiley-VCH: 2000, Weinheim, Germany.

In order to ensure economic use of such biocatalysts, some conditions have to be satisfied: the biocatalyst has to be active for a sufficiently long time under the reaction conditions, it should be readily removable after the end of the reaction and it should be reusable as often as possible. Ideally, these conditions should be satisfied for a very wide range of reaction conditions (for example temperature range, type of solvents used, pressures, etc), in order to provide as universal as possible a catalyst.

In order to satisfy these conditions, it is typically necessary to immobilize the enzymes or microorganisms containing enzymes used.

Frequently, the enzymes or microorganisms containing enzymes are immobilized noncovalently on carriers; the carriers used are frequently ion exchange resins or polymer particles which possess suitable particle size distributions. Examples for this purpose are the commercial products Novozym 435, Lipozym RM IM or Lipozym TL IM from Novozymes A/S, Bagsvaerd, Denmark or Amano PS, from Amano, Japan. These examples are immobilized lipases which find wide use, since such immobilizates also exhibit industrially utilizable activities in nonaqueous systems, i.e. those which comprise only organic solvents, if any, as described, for example, in J. Chem. Soc., Chem. Comm. 1989, 934-935. A disadvantage of the use of such immobilizates is, however, firstly the desorption of the enzyme or of the microorganisms containing enzymes which occurs depending on the reaction system used, for example in the case of use of surfactant components. The loss of activity associated with such a desorption is shown in Comparative Example 1. In addition, such preparations possess inadequate mechanical stability, as a result of which use in simple stirred reactors is possible only with acceptance of significantly restricted reusability, if at all. The mechanical instability of such preparations is shown in Comparative Example 2.

In order to enable the repeated use of such enzyme preparations, other reactor designs therefore have to be used. Eur. J. Lipid Sci. Technol. 2003, 105, 601-607 describes, for example, the use of a fixed bed reactor for performing lipase-catalyzed esterifications. A disadvantage of this process is, however, the restriction to low-viscosity homogeneous reaction mixtures, since high-viscosity mixtures or suspensions cannot be conveyed through a fixed bed.

K. Faber "Biotransformations in Organic Chemistry", Springer: 2000, Berlin, Germany, describes, on page 384 ff., the use of enzymes incorporated into alginates. However, the preparations thus obtained have an exceptionally low mechanical stability and exhibit only low activity in nonaqueous systems.

In addition, the subsequent crosslinking of immobilized enzymes with reactive substances, for example glutaraldehyde, is described. However, a disadvantage is the usually significantly reduced specific activity of the crosslinked preparations compared to the activity before the modification. Furthermore, this process does not make any contribution to improving the mechanical stability.

Likewise described there is the covalent immobilization of enzymes on reactive carriers. A disadvantage here is that suitable functional groups have to be present on the surface of the enzyme, which can react with the carrier; in addition, a loss of enzyme activity is often achieved as the result.

J. Am. Chem. Soc. 1999, 121, 9487-9496 describes the incorporation of enzymes into siloxane matrices, known as sol-gels. A disadvantage of sol-gel preparations is the low particle size distribution which complicates efficient removal by filtration, the lack of mechanical stability, the occurrence of desorption, the use of toxic reactants (for the toxicity of TEOS, see, for example, Nippon Sanso Giho 1990, 9, 68-72 and Archives of Toxicology 1994, 68, 277-283; for the toxicity of TMOS, see, for example, Fundamental and Applied Toxicology 1989, 13, 285-295; for the production of nontoxic sol-gels, laborious steps are necessary, for example storage over 6 months or thermal treatment at 350° C., as described in Polimery w Medycynie 2000, 30, 45-54, and also the swelling behaviour which is very highly dependent upon the solvent used and does not permit universal use in different reaction systems (aqueous and nonaqueous). J. Sol Gel Sci. Technol. 2003, 26, 1183-1187 shows, by way of example, the solvent dependence of the enzyme activity observed and hence the lack of satisfaction of the demand for wide usability.

Landbauforschung Völkenrode, 2002, special edition 241, 41-46 describes sol-gel preparations in which enzymes are first immobilized onto "fine" silicone particles and then encapsulated into a sol-gel. The problem of mechanical stability is thus solved partially, but the experiments described show that sufficient activities are achieved only in selected solvents; use in a solvent-free system is not described at all. In addition, the preparations are not obtained in a directly usable form, but rather first have to be cut to an appropriate size, which is barely implementable on the industrial scale.

J. Mol. Catal. B, 2005, 35, 93-99 describes the immobilization of enzymes by incorporation of aqueous enzyme solutions into mechanically stable silicone spheres, known as static emulsions. The resulting specific activities of the preparations are, though, at up to 33 U/g, much too low compared to the above-described immobilizates on inert carriers, where specific activities of more than 1000 U/g can be achieved easily (U=unit or µmol/min).

WO 03/106607 A1 likewise describes such static emulsions, but exclusively the use in aqueous systems is described; the application is a washing composition, i.e. not a biocatalysis, and the resulting particle sizes, at approx. 10 µm, are too small for efficient filtration out of organic reaction mixtures.

There is therefore still a need for methods of enzyme immobilization which overcome the disadvantages of the prior art, in order to implement biocatalytic processes which have not been realizable to date.

It was therefore an object of the present invention to provide enzyme preparations which do not have one or more of the disadvantages of the prior art preparations. In particular, enzyme preparations shall be provided, which have a high stability with respect to mechanical forces and with respect to desorption and at the same time preferably possess specific activities in different aqueous and nonaqueous reaction mixtures which are high enough to enable industrial use. In terms of their particle size distribution, the enzyme preparations should preferably be capable of being removed from the reaction system in a simple manner and of being reused.

Further objects which are not specified explicitly are evident from the context of the description which follows, the examples and the claims.

It has been found that, surprisingly, this object is achieved by enzyme preparations which are obtained by immobilizing enzymes or microorganisms comprising enzymes on an inert carrier and then coating with a silicone coating obtained by hydrosilylation.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

The present invention therefore provides enzyme preparations which are obtainable by enzyme immobilizates which comprise enzymes or microorganisms containing enzymes immobilized on an inert carrier being provided with a silicone coating obtained by hydrosilylation, and their use as an industrial biocatalyst.

The present invention also provides a process for preparing the inventive enzyme preparations, which is characterized in that enzyme immobilizates which comprise enzymes or microorganisms comprising enzymes immobilized on an inert carrier are provided with a silicone coating obtained by hydrosilylation.

The inventive enzyme preparations have the advantage that they have a high stability with respect to mechanical forces and with respect to desorption. In spite of these improved properties, the inventive enzyme preparations have specific activities in various aqueous reaction mixtures (for example in the hydrolysis of tributyrin) and nonaqueous reaction mixtures (for example in the solvent-free synthesis of propyl laurate), which are high enough to enable industrial use. The inventive enzyme preparations also have the advantage that the selection of the carrier material and of the associated particle size distribution allows the particle size to be adjusted such that simple removal of the enzyme preparations from the reaction system and hence also the reuse of the enzyme preparations is possible.

The inventive enzyme preparations and a process for their production are described below by way of example, without any intention that the invention be restricted to these illustrative embodiments. When ranges, general formulae or compound classes are specified below, these shall not only encompass the corresponding ranges or groups of compounds which are mentioned explicitly but also all sub-ranges and subgroups of compounds which can be obtained by selecting individual values (ranges) or compounds. When documents are cited within the present description, their contents shall be incorporated completely in the disclosure-content of the present invention. When compounds, for example organically modified polysiloxanes which may have different units more than once are described in the context of the present invention, they may occur in these compounds in random distribution (statistical oligomer) or ordered (block oligomer). Information regarding the number of units in such compounds should be interpreted as the mean value, averaged over all appropriate compounds.

The inventive enzyme preparations are notable in that they are obtainable by providing enzyme immobilizates which comprise enzymes or microorganisms comprising enzymes immobilized on an inert carrier with a silicone coating, which is obtained by hydrosilylation.

To produce the enzyme immobilizates, it is possible to use whole cells, resting cells, purified enzymes or cell extracts which comprise the corresponding enzymes, or mixtures thereof. Preference is given to using hydrolytic enzymes, for example lipases, esterases or proteases, for example lipases from *Candida rugosa*, *Candida antarctica*, *Pseudomonas* sp., *Thermomyces langosiosus*, porcine pancreas, *Mucor miehei*, *Alcaligines* sp., cholesterol esterase from *Candida rugosa*, esterase from the porcine liver, more preferably lipases. Accordingly, the enzyme immobilizates preferably comprise enzymes from the class of the hydrolases, preferably lipases.

The inert carriers used may be inert organic or inorganic carriers. The inert carriers used, or present in the enzyme immobilizate, are preferably those particulate carriers which have a particle size distribution in which at least 90% of the particles have a particle size of 10 to 5000 µm, preferably of 50 µm to 2000 µm. Alternatively, the number of particles with these characteristics is selected from the range of from at least 90% to about 95%; from at least 90% to about 99% and from at least 90% to about 99.9%. The organic carriers used may especially be those which comprise or consist of polyacrylate, polymethacrylate, polyvinylstyrene, styrene-divinylbenzene copolymers, polypropylene, polyethylene, polyethylene terephthalate, PTFE and/or other polymers. The carrier materials used may, depending on the enzyme to be immobilized, especially be acidic or basic ion exchange resins, for example Duolite A568, Duolite XAD 761, Duolite XAD 1180, Duolite XAD 7HP, Amberlite IR 120, Amberlite IR 400, Amberlite CG 50, Amberlyst 15 (all products from Rohm and Haas) or Lewatit CNP 105 and Lewatit VP OC 1600 (products from Lanxess, Leverkusen, Germany). The inorganic carriers used may be oxidic and/or ceramic carriers known from the prior art. In particular, the inorganic carriers used may, for example, be Celite, zeolites, silica, controlled-pore glass (CPG) or other carriers, as described, for example, in L. Cao, "Carrier-bound Immobilized Enzymes: Principles, Application and Design", Wiley-VCH: 2005, Weinheim, Germany. More preferably, the inert carriers present in the enzyme immobilizate or the inert carriers used to produce the enzyme immobilizates consist of polyvinylstyrene, polymethacrylate or polyacrylate.

The immobilization on the particles can, in accordance with the invention, be effected covalently or noncovalently, preferably noncovalently. For noncovalent immobilization, the carrier can be incubated or impregnated, for example, with an aqueous enzyme solution which may optionally comprise further constituents, for example inorganic salts or detergents. This incubation/impregnation can be carried out, for example, at temperatures between 0° C. and 50° C., preferably between 0° C. and 40° C. Preference is given to effecting the incubation/impregnation over a period of a few minutes to a few hours. The progress of the incubation can be followed by determining the concentration of the enzyme in the solution with the common methods for protein determination. On attainment of the desired degree of immobilization, the carrier can preferably be washed with water and, if desired, dried. An enzyme immobilizate obtained in this way can subsequently be provided with a silicone coating in accordance with the invention.

According to the invention, it is, however, also possible to use enzyme immobilizates which are commercially available, for example Novozym 435, Lipozym RM IM or Lipozym TL IM from Novozymes A/S, Bagsvaerd, Denmark, or Amano PS from Amano, Japan.

According to the invention, the silicone coating is obtained by hydrosilylation. To this end, preferably Si—H-functional polysiloxanes are reacted in the presence of catalysts, preferably of transition metal catalysts, with organically modified polysiloxanes which possess at least one terminal carbon-carbon double bond, preferably at least two carbon-carbon double bonds.

The Si—H-functional polysiloxanes used are preferably SiH polysiloxanes of the general formula I

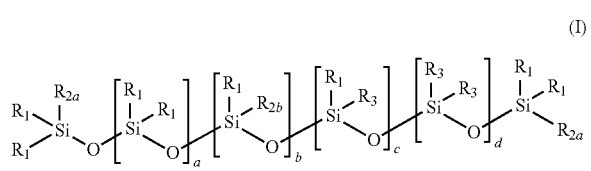

(I)

where
N=a+b+c+d+2=3 to 850, preferably 6 to 160,
a=1 to 800, preferably 2 to 150,
b=0 to 400, preferably 2 to 75,
c=0 to 10, preferably 0,
d=0 to 10, preferably 0,
$R_1$ are independently the same or different, and are selected from the group comprising: saturated or unsaturated, optionally branched alkyl groups having 1 to 30 carbon atoms, alkaryl radicals having 7 to 30 carbon atoms, aryl radicals having 6 to 30 carbon atoms, preferably alkyl groups having 1 to 4 carbon atoms or phenyl, especially methyl;
$R_{2a}$ are independently hydrogen or $R_1$;
$R_{2b}$ are independently hydrogen or $R_1$;
$R_3$ are independently identical or different radicals of the general formula Ia

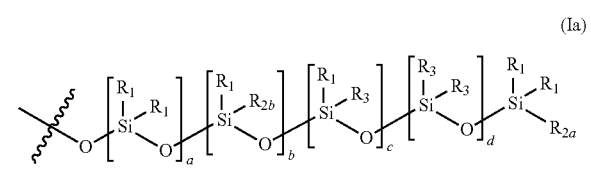

(Ia)

where
N=a+b+c+d+2=3 to 850, preferably 6 to 160,
a=1 to 800, preferably 2 to 150,
b=0 to 400, preferably 2 to 75,
c=0 to 10, preferably 0,
d=0 to 10, preferably 0,
$R_1$ are independently the same or different, and are selected from the group comprising: saturated or unsaturated, optionally branched alkyl groups having 1 to 30 carbon atoms, alkaryl radicals having 7 to 30 carbon atoms, aryl radicals having 6 to 30 carbon atoms, preferably alkyl groups having 1 to 4 carbon atoms or phenyl, especially methyl;
$R_{2a}$ are independently hydrogen or $R_1$;
$R_{2b}$ are independently hydrogen or $R_1$;
$R_3$ are independently identical or different radicals of the formula Ia or an $R_1$ radical.

Preference is given to using, as the SiH-functional polysiloxane, a polysiloxane of the general formula I

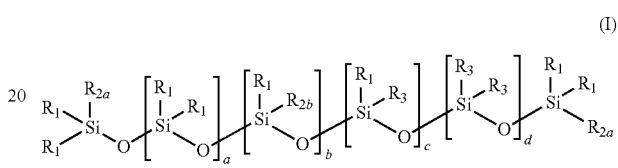

(I)

where
N=a+b+c+d+2=6 to 160,
a=2 to 150,
b=2 to 75,
c=0,
d=0,
$R_1$ are independently the same or different, and are selected from the group comprising: saturated or unsaturated, optionally branched alkyl groups having 1 to 30 carbon atoms, alkaryl radicals having 7 to 30 carbon atoms, aryl radicals having 6 to 30 carbon atoms, preferably alkyl groups having 1 to 4 carbon atoms or phenyl, especially methyl;
$R_{2a}$ are independently hydrogen or $R_1$;
$R_{2b}$ are independently hydrogen or $R_1$.

It is well known to the person skilled in the art that the compounds are or may be present in the form of a mixture with a distribution controlled essentially by statistical laws. The values for the indices a, b, c and d are therefore typically mean values.

According to the invention, the olefinic reactants, i.e. the polysiloxanes containing a terminal carbon-carbon double bond, are preferably polysiloxanes of the general formula II:

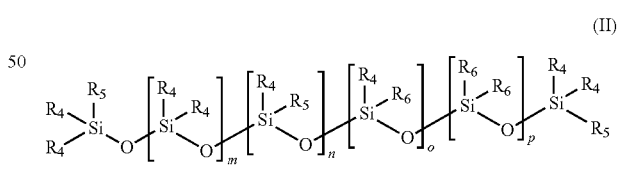

(II)

where
N=m+n+o+p+2=3 to 1000, preferably 10 to 600,
m=1 to 800, preferably 2 to 600,
n=0 to 20, preferably 0 to 10, more preferably 0,
o=0 to 10, preferably 0,
p=0 to 10, preferably 0,
$R_4$ are independently the same or different and are from the following group: saturated or unsaturated, optionally branched alkyl groups having 1 to 30 carbon atoms, alkaryl radicals having 7 to 30 carbon atoms, aryl radicals having 6 to 30 carbon atoms, preferably alkyl groups having 1 to 4 carbon atoms or phenyl, especially methyl;

$R_5$ are independently a terminally unsaturated alkyl radical, preferably vinyl, or an alkoxy radical, preferably having 3 to 20 carbon atoms, or $R_4$;

$R_6$ are independently identical or different radicals of the general formula IIa

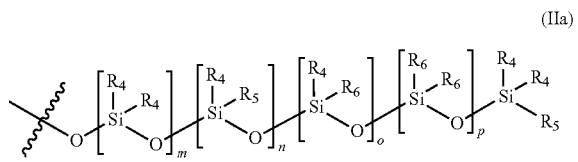

(IIa)

where $N=m+n+o+p+2=3$ to 1000, preferably 10 to 600, $m=1$ to 800, preferably 2 to 600, $n=0$ to 20, preferably 0 to 10, more preferably 0, $o=0$ to 10, preferably 0, $p=0$ to 10, preferably 0, $R_4$ are independently the same or different and are from the following group: saturated or unsaturated, optionally branched alkyl groups having 1 to 30 carbon atoms, alkaryl radicals having 7 to 30 carbon atoms, aryl radicals having 6 to 30 carbon atoms, preferably alkyl groups having 1 to 4 carbon atoms or phenyl, especially methyl;

$R_5$ are independently a terminally unsaturated alkyl radical, preferably vinyl, or an alkoxy radical, preferably having 3 to 20 carbon atoms, or $R_4$;

$R_6$ are independently identical or different radicals of the general formula IIa or $R_4$ radicals.

The polysiloxanes containing a terminal carbon-carbon double bond used are preferably polysiloxanes of the general formula II:

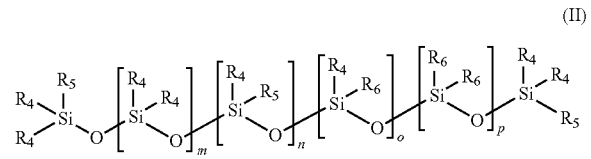

(II)

where $N=m+n+o+p+2=10$ to 600, $m=2$ to 600, $n=0$, $o=0$, $p=0$, $R_4$ are independently the same or different and are from the following group: saturated or unsaturated, optionally branched alkyl groups having 1 to 30 carbon atoms, alkaryl radicals having 7 to 30 carbon atoms, aryl radicals having 6 to 30 carbon atoms, preferably alkyl groups having 1 to 4 carbon atoms or phenyl, especially methyl;

$R_5$ are independently a terminally unsaturated alkyl radical, preferably vinyl, or an alkoxy radical, preferably having 3 to 20 carbon atoms.

It is well known to the person skilled in the art that the compounds of the formula II are or may be present in the form of a mixture with a distribution controlled essentially by statistical laws. The values of the indices m, n, o and p are therefore typically mean values.

The hydrosilylation can be carried out by established methods in the presence of a catalyst. It is possible, for example, to use catalysts which are typically used for hydrosilylations, for example platinum, rhodium, osmium, ruthenium, palladium, iridium complexes or similar compounds or the corresponding pure elements or their derivatives immobilized on silica, alumina or activated carbon or similar carrier materials. Preference is given to performing the hydrosilylation in the presence of Pt catalysts such as cisplatin or Karstedt catalyst [tris(divinyltetramethyldisiloxane)-bis-platinum].

The amount of catalyst used is preferably $10^{-7}$ to $10^{-1}$ mol per mole of olefin or per mole of terminal carbon-carbon double bond, preferably 1 to 100 ppm. The hydrosilylation is carried out preferably at temperatures of 0 to 200° C., preferably of 20 to 120° C.

The hydrosilylation can be carried out in the presence or absence of solvent. Generally, solvents are not needed for the performance of the reaction. The reaction can, however, be carried out in suitable solvents, for example aliphatic or aromatic hydrocarbons, cyclic oligosiloxanes, alcohols or esters. Suitable solvents are especially cyclohexane or toluene.

According to the invention, based on the mass of the carrier used, preferably 1 to 500% by mass, more preferably 10 to 200% by mass, especially preferably 20 to 150% by mass, of siloxane components are used. The siloxane components are composed especially of the sum total of the compounds of the formula I and II and of their reaction products.

The hydrosilylation can be carried out using a wide variety of different ratios of the compounds of the formulae I to compounds of the formulae II. Preference is given to effecting the hydrosilylation at a molar ratio based on the reactive groups of 1:10 to 10:1, more preferably of 1:5 to 5:1, especially preferably of 1:1.1 to 1.1:1 and most preferably of 1:1. Selection of the compounds of the general formula I and II used and variation in their mixing ratios allows the properties of the silicone coating to be tailored in relation to perviousness for substrates and other reaction properties. Selection of the weight ratio of silicone components to enzyme immobilizates allows the layer thicknesses of the silicone coating to be varied and to be adjusted to appropriate requirements.

The inventive silicone coating, produced by hydrosilylation, can be obtained by carrying out the hydrosilylation in the presence of the enzyme immobilizates. However, it is also possible to obtain the coatings by applying a siloxane obtained by hydrosilylation subsequently to the enzyme immobilizates. This can be effected, for example, by treating the enzyme immobilizates with a solution of the siloxane, for example a solution of the siloxane in an organic solvent, especially cyclohexane or toluene. Subsequently, the solvent can be removed, for example, by evaporation. The concentration of siloxane in such a solution is preferably 10 to 100% by mass, more preferably 30 to 100% by mass. However, preference is given to obtaining the inventive silicone coating by carrying out the hydrosilylation in the presence of the enzyme immobilizates.

The inventive enzyme preparations are preferably prepared by the process according to the invention described below. This process for preparing enzyme preparations is notable in that enzyme immobilizates which comprise enzymes or microorganisms comprising enzymes immobilized on an inert carrier are provided with a silicone coating obtained by hydrosilylation.

Preference is given to performing the process according to the invention in such a way that the enzyme immobilizates are provided with a silicone coating by contacting the enzyme immobilizates with a reaction mixture which comprises SiH-functional polysiloxanes, polysiloxanes containing terminal carbon-carbon double bonds and a catalyst which catalyzes the hydrosilylation under hydrosilylation conditions. In particular, the process can be performed in such a way that a hydrosilylation reaction is carried out in the presence of enzyme immobilizates which comprise enzymes or microorganisms comprising enzymes immobilized on an inert carrier. The silicone formed in the hydrosilylation allows the enzyme immobilizate to be provided with a silicone coating.

The hydrosilylation can be carried out in a manner known to those skilled in the art. Preference is given to performing the hydrosilylation using the abovementioned parameters/feedstocks/catalysts.

In a preferred embodiment of the process according to the invention, a particular amount of enzyme immobilizate is admixed with a mixture (reaction mixture) of the silicone reagents (compounds of the formulae I and II plus catalyst), for example by adding a mixture comprising compounds of the general formula I and of the general formula II and Karstedt catalyst. For example, it is possible to add to 1 g of an enzyme immobilizate a mixture of compounds of the formula I and II in a molar mixing ratio of 10:1 to 1:10, and also Karstedt catalyst, for example 50 ppm based on the amount of silicone components present. For the purpose of optimizing the coating properties, it may be advantageous to dissolve the silicone components including the catalyst, before the addition, in a solvent, for example cyclohexane, toluene or another organic solvent, and then to add the solution to the enzyme immobilizate. When, for example, cyclohexane is used as the solvent, it has been found to be advantageous, after addition of the solution to the enzyme immobilizates, to strongly disperse this mixture for approx. 15 to 30 min, for example by means of a vortexer (Ika, level 9), until the bulk of the cyclohexane has evaporated off. Subsequently, the resulting enzyme preparations are dried, i.e. hardened, in a drying cabinet at 50° C., for example for 12 hours. Altering the mixing ratios of the compounds of the general formula I and II allows the properties of the silicone coating to be varied without any problem and adjusted to appropriate requirements.

A further embodiment of the process according to the invention differs from the above embodiment in that the enzyme immobilizates to be coated are immersed into the desired reaction mixture, then removed from the reaction mixture and dried. The removal can be effected, for example, using a screen which retains the enzyme immobilizate particles. The immersion time is preferably 1 to 10 minutes. The drying can be effected in a conventional drying cabinet. Preference is given to effecting the drying/hardening at a temperature of 20° C. to 80° C., preferably at 40° C. to 60° C., more preferably at approx. 50° C.

In a further embodiment of the process according to the invention, which is suitable especially for performance on the industrial scale, the hydrosilylation is carried out using a pelletizing pan unit (for example from Erweka or Eirich). In this case, a defined amount of enzyme immobilizate particles is introduced into the so-called pan unit and stirred. Subsequently, either the mixture comprising compounds of the formulae I and II, and also catalyst and also if appropriate solvent, is added or else, preferably, using a two-substance nozzle (for example from Schlick or others), in which the mixture or the components is/are applied under pressure (for example nitrogen or synthetic air) in the form of a fine droplet mist, in order to ensure a very homogeneous distribution on the particles. After a prolonged coating time, the particles are removed as described above and dried, i.e. hardened, for a few hours at a temperature of 20° C. to 80° C., preferably of 40° C. to 60° C., more preferably of 50° C., in a drying cabinet, and can then be stored at room temperature until further use.

In a further embodiment, the particles can be generated in a fluidized bed reactor (for example from Erweka), in which particles and the reaction mixture are applied with high dispersion in appropriate mixing ratios.

The inventive enzyme preparations can be used, for example, as biocatalysts, especially as industrial biocatalysts.

In another embodiment of the invention, the inventive enzyme preparations exhibit an enhanced mechanical stability after formation of an enzyme suspension as measured by the relative % decrease in particle size distribution. In one embodiment of this aspect of the invention, the relative % decrease ranges from about 5% to about 15%; in another embodiment of this aspect of the invention, the relative % decrease ranges from about 2.5% to about 10%.

Another means of characterizing the decrease is by relation to the decrease observed with uncoated enzyme. In this means of characterizing the relative % decrease in particle size, the decrease for the coated preparations of the invention is only about 40% to about 90% of the total decrease of uncoated preparations. In another embodiment of this aspect of the invention, the decrease for the coated preparations of the invention is only about 50% to about 80% of the total decrease of uncoated preparations.

In another embodiment of the invention, the amount of protein desorbed for the enzyme preparations of the invention when subjected to harsh reaction conditions exhibits about 50% to about 99% less desorption than an uncoated enzyme preparation. In another embodiment of the invention, there is about 65% to about 90% less desorption than an uncoated enzyme preparation.

The present invention is illustrated in detail with reference to FIGS. 1 and 2, without being restricted thereto.

BRIEF DESCRIPTION OF THE DRAWINGS

FIG. 1 shows that the stirred suspension based on untreated NZ435 is cloudy as a result of fine particles. The stirred suspension based on NZ435 treated in accordance with the invention, in contrast, is clear, i.e. comprises no particles or at least no particles in a visible size (FIG. 2).

Figure 1:
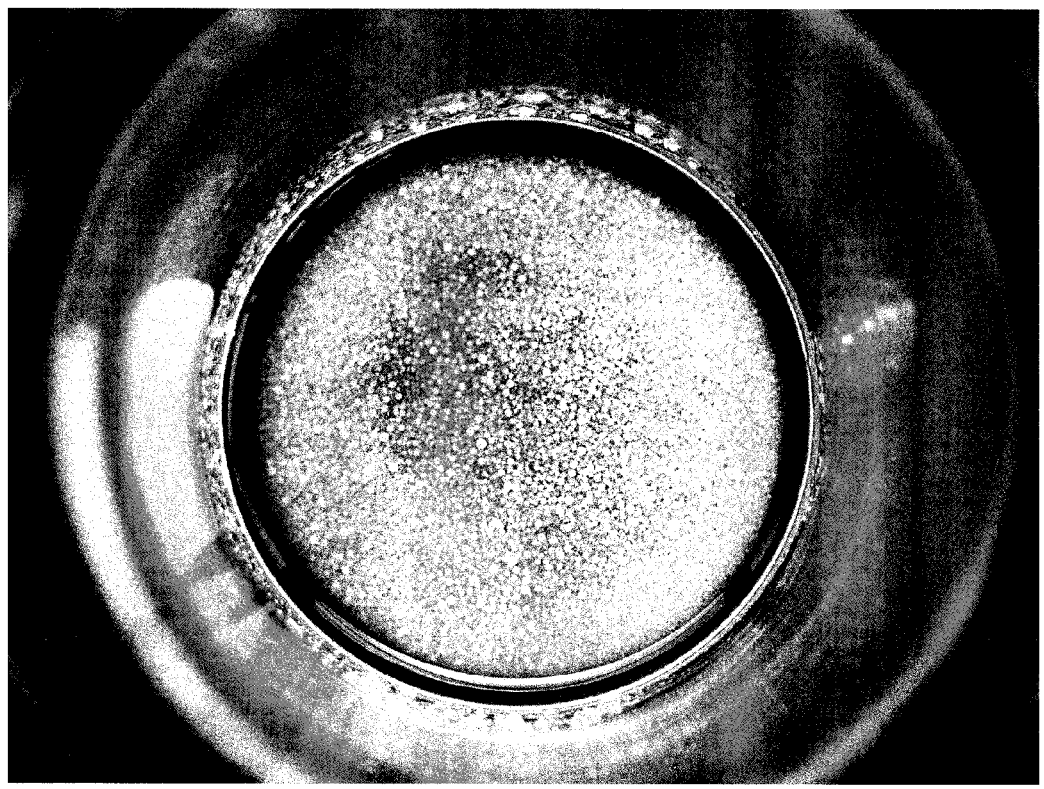
FIGS. 1 and 2 show images of stirred suspensions in a 100 ml beaker with a diameter of the base of 4 cm. The suspensions have been produced as described in Example 2.

The examples which follow are intended to illustrate the present invention in detail, without restricting the scope of protection which is evident from the description and the claims.

EXAMPLES

Materials and Methods

Novozym 435 (NZ435) is a commercial enzyme immobilizate from Novozymes A/S, Bagsvaerd, Denmark, a lipase B from *C. antarctica* immobilized on a polymethacrylate by adsorption.

Hydrolytic Activity (Tributyrin Hydrolysis in Aqueous Medium):

The hydrolytic activity was determined by the so-called pH-stat method. In this method, the acid released in the hydrolysis is titrated against a base, such that the pH of the solution is kept constant. The time dependence of the consumption of base allows the acid released, and hence the enzyme activity, to be quantified. Illustrative procedure: 10-20 mg of catalytically active particles were added to 25 ml of Tris-HCl buffer (1 mM, pH 7.5; additionally contains 0.1 mM NaCl and $CaCl_2$) and 500 μl of tributyrin were added.

The hydrolytic activity was quantified on an autotitrator (Tritroline alpha, from Schott) via the amount of base titrated in (50 MM NaOH).

Hydrolytic Activity (Ethyl Valerate in Aqueous Medium):

Analogously to the determination of the hydrolysis activity using the example of tributyrin, ethyl valerate can also be used. Illustrative procedure: 10-20 mg of catalytically active particles were added to 25 ml of phosphate buffer (1 mM, pH 8.0) and 500 µl of ethyl valerate. The hydrolytic activity was quantified on an autotitrator (Tritroline alpha, from Schott) via the amount of base titrated in (10 mM NaOH).

Synthesis Activity in PLU Units (Propyl Laurate Synthesis Activity in Solvent-Free System):

10 mg of catalytically active particles were added to 5 ml of equimolar substrate solution (lauric acid and 1-propanol) and incubated while shaking and/or stirring at 60° C. Samples ($V_{sample}$: 50 µl) were taken every 5 min over 25 min and transferred into 950 µl of decane (internal standard: 4 mM dodecane). The PLUs were determined with reference to the initial product formation rates. Propyl laurate was detected by gas chromatography (retention time: 9.791 min) (Shimadzu 2010, BTX column from SGE; length 25 m, I.D. 0.22 µm; film: 0.25 µm; detector type: FID at 300° C.; injector temperature 275° C. and injection volume 1 µl, split ratio 35.0; carrier gas pressure (helium) 150 kPa; temperature programme: start temperature 60° C., hold for 1.5 min, temperature rise 20° C./min, end temperature 250° C., hold for 2.5 min).

Determination of Laccase Activity:

To determine laccase activity, catalytically active particles (native or immobilized laccase) are transferred into 19 ml of potassium phosphate buffer (100 mM, pH 6, 37° C.) with 1 ml of ABTS solution (ready-to-use solution, 1.8 mM, available from Sigma-Aldrich) and the increased extinction is measured photospectro-metrically at 405 nm. Laccase activity shall be monitored over a period of 20 min. The samples are taken at intervals of 5 min. The activity can be determined as follows:

$$\text{activity} = \frac{\Delta Ext._{405} \cdot V_{total}}{\Delta t \cdot \varepsilon \cdot d \cdot V_{sample}}$$

$\Delta Ext._{405}$ change in extinction as a function of time
$V_{total}$ total volume of reaction batch [20 ml]
$V_{sample}$ volume of sample [2 ml]
$\Delta t$ change in time [min]
$\varepsilon$ extinction coefficient for ABTS at 405 nm [43.2 ml µmol$^{-1}$ cm$^{-1}$]
d path length of cell [1 cm]

The activity is reported in units (U/ml or U/g) defined as 1 µmol of substrate conversion per minute.

Protein Determination According to Bradford:

The determination of the protein content in the supernatant was carried out according to the method of Bradford (Anal. Chem. 1976, 72, 248-254), which is based on the binding of the triarylmethane dye Coomassie Brilliant Blue G-250 to basic and aromatic amino acid residues in the protein. This binding causes a shift in the absorption maximum from 465 nm to 595 nm. To establish the calibration, the absorbances of BSA were determined in the concentrations of 5-20 µg/l. To this end, the particular samples were made up to 800 µl with $H_2O$, and 200 µl of Bradford reagent (Bio Rad, Munich) were added, and the samples were measured at 595 nm.

To determine the leaching behaviour of the catalytically active particles under harsh reaction conditions, the procedure was extended by the following steps:

The protein content of Novozym 435 (NZ435) was determined by the following scheme. The NZ435 particles were incubated with shaking at 45° C. in acetonitrile/$H_2O$ (1:1, v/v) for 30 min, and then samples (for example 1 ml) were taken from the supernatant, lyophilized and resuspended in $H_2O$ (likewise 1 ml). Subsequently, the protein content was determined as described above. The results can be taken from Table 1.

TABLE 1

Test results for the untreated enzyme immobilizate

| Native (without coating) | Hydrolytic activity [U/mg] | PLU [U/g] | Amount of desorbed protein [µg of protein/mg of NZ435] | Amount of desorbed protein [%] |
|---|---|---|---|---|
| NZ435 | 1.05 ± 0.15 | 8000 ± 500 | 56 ± 1 | 5.6 |

Comparative Example 1

Determination of the Mechanical Stability of Conventional Enzyme Immobilizates

For the purpose of determining the mechanical stabilities of the particles, they were incubated in various high-viscosity equimolar substrate solutions (for example polyethylene glycol (molar mass approx. 2400) and oleic acid) with high power inputs and at temperatures of >60° C., and then the integrity of the particles was studied. Using NZ435 (5% by weight in polyethylene glycol (molar mass approx. 2400) and oleic acid), the formation of fine particles could be detected with the naked eye after 24 hours, for example by virtue of clear occurrence of turbidity.

Comparative Example 2

Determination of the Desorption Stability of Conventional Enzyme Immobilizates

For the purpose of determining the desorption stability of the particles under harsh reaction conditions, fractions of 50 mg of NZ435 were shaken in 20 ml of MeCN/$H_2O$ (1:1, v/v) solution at 45° C. for 30 min. Defined samples (for example 1 ml) were taken from the supernatant and the protein content in the supernatant was determined as described above. The particles were recovered by means of a fluted filter and washed with 100 ml of $H_2O$, and dried at 50° C. for 12 h, in order then to determine the hydrolytic activity and the synthesis activity in PLU according to the scheme described above. The results can be taken from Table 2.

TABLE 2

Test results for Comparative Example 2

| Native (without coating) | Hydrolytic activity [U/mg] | Synthesis activity [PLU/g] | Amount of protein desorbed [μg of protein/mg of NZ435] |
|---|---|---|---|
| NZ435 | 0* | 0* | 56 |

*In the above-described activity tests, no activity was quantifiable.

The invention is further described by the following non-limiting examples which further illustrate the invention, and are not intended, nor should they be interpreted to, limit the scope of the invention.

Example 1

Production of a Stable Enzyme Preparation

Illustrative preparation:

1 g of NZ435 particles were admixed in a metal dish with 1 ml of reaction mixture, consisting of various compositions of compounds of the general formulae I and II (for composition see Table 3; the components of the general formulae I and II were prepared by processes familiar to those skilled in the art, as described, for example, in U.S. Pat. No. 7,196,153 B2, by equilibration), and Karstedt catalyst (Syloff 4000, product from Dow Corning, USA). The silicone components including the catalyst were in each case dissolved in 3 ml of cyclohexane before the application and then added to the particles in the metal dish. The addition was followed immediately by strong dispersion by means of a vortexer (Ika, level 9) for 15-30 min until the bulk of the cyclohexane had evaporated off. Subsequently, the particles were dried at 50° C. in a drying cabinet for about 12 h.

The particles produced by this process, compared to the untreated immobilizate, have activity yields in the hydrolysis of up to 73% (Examples 1 i and 1 iii, 0.77 U/mg of NZ435 compared to 1.05 U/mg for untreated NZ435, as described in Comparative Example 1), or 65% (Example 1 i, 0.68 U/mg of NZ435). In the synthesis, activity yields of 94% (Example 1 i), 84% (Example 1 iii) or 68% (Example 1 ii) were achieved.

Example 2

Determination of the Mechanical Stability of Inventive Enzyme Preparations 300 mg of particles (untreated, native NZ435 or NZ435 treated according to iii in Table 3) were each stirred vigorously at 60° C. in 5 ml of lauric acid for 90 min (magnetic stirrer plate from Ika, RT Power model, level 5, stirrer bar: length 3.1 cm, width 0.6 cm). After the stirrer had been removed, photographs of the stirred suspensions were taken (FIGS. 1 and 2).

Figure 2:
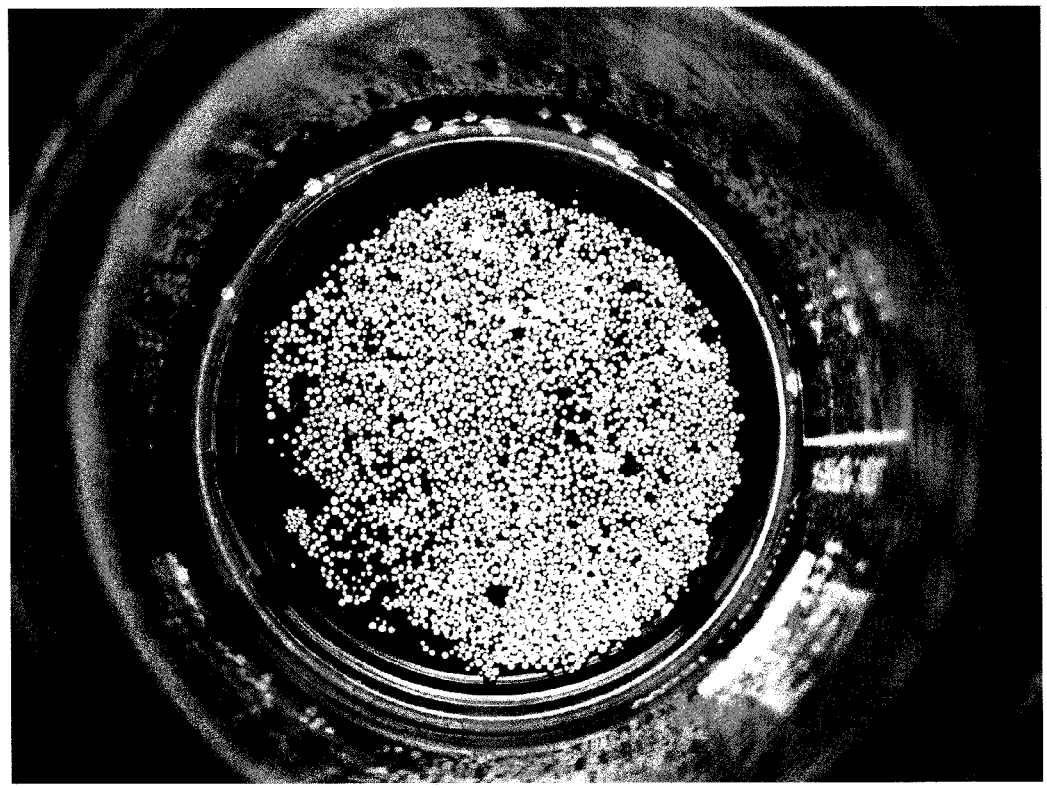

FIG. 1 shows clearly that the stirred suspension based on untreated NZ435 is cloudy as a result of fine particles. The stirred suspension based on NZ435 treated in accordance with the invention, in contrast, is clear, i.e. comprises no particles or at least no particles in a visible size (FIG. 2).

Subsequently, the particles were removed from the suspensions by means of a fluted filter, rinsed with approx. 10 ml of acetone and dried at 50° C. for 12 h.

For the purpose of determining the mechanical stability of the particles, a determination of the particle size distribution was carried out. The screen fractions used here had the following exclusion sizes: 800 μm, 500 μm, 300 μm, 150 μm and 75 μm. By screening, the particle size distributions before and after stirring were determined. The results can be taken from Table 4.

TABLE 3

Composition of the various coated particles

| No. | Initial weight of NZ435 | Component of general formula I; c = d = 0; R1 = R2a = methyl, R2b = H | Component of general formula II; b = c = d = 0; R4 = methyl, R5 = vinyl | Proportion of NZ435 [%] | Hydrolysis activity [U/mg of immob. (U/mg of NZ435)] | Synthesis activity [PLU/g of immob. (PLU/g of NZ435)] |
|---|---|---|---|---|---|---|
| NZ435[1] | 1 g | — | — | 100 | 1.05 | 8000 (8000) |
| i | 1 g | a = 43, b = 5 100 μl | a = 98 900 μl | 57.4 | 0.44 (0.77) | 4300 (7500) |
| ii | 1 g | a = 64.5, b = 3.5 300 μl | a = 98 700 μl | 57 | 0.39 (0.68) | 3100 (5400) |
| iii | 1 g | a = 43, b = 5 100 μl | a = 348 900 μl | 57.4 | 0.44 (0.77) | 3800 (6700) |

[1]data for untreated, native immobilizate, see Comparative Example 1

TABLE 4

Mean particle size distribution (PSD) of uncoated NZ435 and coated NZ435.

| | Component of general formula I; c = d = 0; R1 = R2a = methyl, R2b = H | Component of general formula II; b = c = d = 0; R4 = methyl, R5 = vinyl | Proportion of NZ435 [% w/w] | PSD before [μm] | PSD after [μm] | Relative decrease in PSD [%] |
|---|---|---|---|---|---|---|
| Native NZ435 | — | — | 100 | 392 | 293 | 25 |
| Coated NZ435 | a = 43, b = 5 100 μl | a = 98 900 μl | 57.4 | 547 | 501 | 8.5 |
| Coated NZ435 | a = 64.5, b = 3.5 300 μl | a = 98 700 μl | 57 | 486 | 458 | 5.8 |
| Coated NZ435 | a = 43, b = 5 100 μl | a = 348 900 μl | 57.4 | 491 | 432 | 12 |

Example 3

Determination of the Desorption Stability of Stable Enzyme Preparations

Analogously to Comparative Example 2, the particles obtained from Example 1 were treated with water/acetonitrile and then the hydrolysis activity, the synthesis activity and the amount of protein released were determined. The result of this determination can be taken from Table 5.

TABLE 5

Results from Example 3

| Sample | Hydrolysis activity [U/mg of immob. (U/mg of NZ435)] | Synthesis activity [PLU/g of immob. (PLU/g of NZ435)] | Amount of protein desorbed [μg/mg of immob. (μg/mg of NZ435)] |
|---|---|---|---|
| NZ435 native (Comparative Example 1) | 1.05 (1.05) | 8000 (8000) | — |
| NZ435 uncoated (Comparative Example 2) | 0 | 0 | 56 |
| i | 0.25 | 1182 ± 13 | 10 |
| ii | 0.29 (0.44) | 1699 ± 24 (2059) | 4.5 (17) |
| iii | 0.28 (0.51) | 1235 ± 54.3 (2980) | 9 (7.9) |
| | (0.49) | (2152) | (16) |

While untreated native enzyme immobilizate after incubation exhibits no hydrolysis activity whatsoever and 56 μg/mg of immobilizate were detectable as free protein, the silicone-coated particles exhibit hydrolysis activities of up to 75% of the starting activity (sample ii, 0.51 U/mg of NZ435 vs. 0.77 U/mg of NZ435 before leaching), synthesis activities of up to 55% of the starting activity (sample ii, 2980 U/g of NZ435 vs. 5400 U/g of NZ435 before leaching), and an enzyme desorption reduced by up to 86% (sample ii).

Example 4

Production of an Enzyme Immobilizate 1 g of Lewatit VPOC1600 (from Lanxess) was stirred at room temperature in 5 ml of CALB solution (Lipozym CALB L, Novozymes A/S, Bagsvaerd, Denmark, hydrolytic activity: 2700 U/ml) for approx. 18 h, removed by means of a fluted filter and rinsed with 250 ml of distilled water, then dried under air for 3 h, rinsed with 1 ml of isopropanol and dried under air once more for 1 h. The immobilizates thus produced were stored in closable reaction vessels at 4° C. until further use.

The activities of the enzyme immobilizates were measured by processes described above (hydrolytic activity of 1.04 U/mg and a synthesis activity of 6000 PLU/g). The loading density was determined by means of a Bradford test to be about 30 $\mu g_{protein}/mg_{VPOC1600}$.

The enzyme immobilizates thus generated were coated with silicone in a second step by the process described above (composition as in test i in Tab. 3). The proportion by mass of enzyme immobilizate in the preparation corresponds to 63%. The hydrolytic activity of the coated preparations is 0.43 U/mg and the synthesis activity 2927 PLU/g.

Analogously to Comparative Example 2, the uncoated particles and the silicone-coated particles were treated with water/acetonitrile and then the hydrolysis activity, the synthesis activity and the amount of protein released were determined. The result can be taken from Table 6.

TABLE 6

Results from Example 4

| Sample | Component of the general formula I; c = d = 0; R1 = R2a = methyl, R2b = H | Component of the general formula II; b = c = d = 0; R4 = methyl, R5 = vinyl | Hydrolysis activity [U/mg of immob. (U/mg native immob.)] | Synthesis activity [PLU/g of immob. (PLU/g of native immob.)] | Amount of protein desorbed [μg/mg of immob. (μg/mg of native immob.)] |
|---|---|---|---|---|---|
| CALB on VPOC1600, uncoated, fresh | — | — | 1.04 | 6000 | — |

TABLE 6-continued

Results from Example 4

| Sample | Component of the general formula I; c = d = 0; R1 = R2a = methyl, R2b = H | Component of the general formula II; b = c = d = 0; R4 = methyl, R5 = vinyl | Hydrolysis activity [U/mg of immob. (U/mg native immob.)] | Synthesis activity [PLU/g of immob. (PLU/g of native immob.)] | Amount of protein desorbed [µg/mg of immob. (µg/mg of native immob.)] |
|---|---|---|---|---|---|
| CALB on VPOC1600, coated, fresh | A = 43, b = 5 100 µL | a = 348 900 µL | 0.43 (0.68) | 2930 (4650) | — |
| CALB on VPOC1600, uncoated after desorption. | — | — | 0 | 0 | 27 ± 5 |
| CALB on VPOC1600 coated after desorption | A = 43, b = 5 100 µL | a = 348 900 µL | 0.234 ± 0.005 (0.37) | 1765 ± 369 (2800) | 3 ± 1.3 (4.7) |

As can be discerned from Table 6, nine times the amount of protein is desorbed in the case of the untreated immobilizate. At the same time, activity yields of 54% (hydrolysis activity) and 60% (synthesis activity) can be achieved. The suitability of the above-described method for coating enzyme immobilizates with silicones, which has already been shown for commercial finished preparations using NZ435, has accordingly also been demonstrated for self-loaded enzyme immobilizates.

Example 5

Determination of Enzyme Activities in Organic Solvent

The activity of the enzyme preparations of Examples 1 and 4, and also of the corresponding native immobilizates is determined by performing a propyl laurate synthesis in methylcyclohexane (starting concentration of substrates=10 mM, T=25° C.).

TABLE 7

Synthesis activity (PLU/g) in methylcyclohexane

| No. | Initial weight of NZ435 | Component of gen. formula I; c = d = 0; R1 = R2a = methyl, R2b = H | Component of gen. formula II; b = c = d = 0; R4 = methyl, R5 = vinyl | Proportion of native NZ435 [% w/w] | Activity [U/g of immob. (U/mg of native immob.)] | Activity after desorption [U/g of immob. (U/g of native immob.)] |
|---|---|---|---|---|---|---|
| NZ435 native | 1 g | — | — | 100 | 581 | 0 |
| i from Example 1 | 1 g | a = 43, b = 5 100 µL | a = 98 900 µL | 57.4 | 227 (395) | 142 (247) |
| ii from Example 1 | 1 g | a = 64.5, b = 3.5 300 µL | a = 98 700 µL | 57 | 240 (421) | 141 (247) |
| iii from Example 1 | 1 g | a = 43, b = 5 100 µL | a = 348 900 µL | 57.4 | 267 (465) | 133 (232) |
| CALB on VPOC1600 native | 1 g | — | — | 100 | 311 | 0 |
| CALB on VPOC1600 coated | 1 g | a = 43, b = 5 100 µL | a = 98 900 µL | 51 | 151 (296) | 118 (231) |

It is clear from Table 7 that the activity yield of the enzyme preparations on use in organic solvent is excellent and that the desorption stability likewise becomes clear.

Example 6

Production of Further Lipase Preparations

Analogously to Example 1 Lipozym RM IM (lipase from *M. miehei*, immobilized on Duolite A568 from Lanxess, available from Novozymes A/S) is provided with a siloxam coating and the activity yield is determined analogously to Example 5 in organic solvent.

TABLE 8

Determination of activity of coated lipase Lipozym RM IM

| Designation | Initial weight of RM IM | Component of gen. formula I; $c = d = 0$; $R1 = R2a =$ methyl, $R2b = H$ | Component of gen. formula II; $b = c = d = 0$; $R4 =$ methyl, $R5 =$ vinyl | Proportion of native immobil. [% w/w] | PLUs in org. solvent |
|---|---|---|---|---|---|
| RM IM native | 1 g | — | — | 100 | 321 ± 40 |
| RM IM coated | 1 g | $a = 43, b = 5$ 100 μL | $a = 98$ 900 μL | 51 | 171 ± 5 |

It is clear from Table 8 that, based on the amount of Lipozym RM IM used, a quantitative activity yield is achieved within the margin of error.

Example 7

Production of Further Lipase Preparations

Analogously to Example 4, a lipase from *T. lanuginosa* (available as Esterase TL01 from Asa Spezialenzyme, comprising a lipase with additional esterase function) is immobilized on Lewatit VPOC1600 and provided with a siloxane coating. Activity is determined by determining the ethyl valerate hydrolysis.

TABLE 9

Results from Example 5

| | Initial weight of native immobil. | Component of gen. formula I; $c = d = 0$; $R1 = R2a =$ methyl, $R2b = H$ | Component of gen. formula II; $b = c = d = 0$; $R4 =$ methyl, $R5 =$ vinyl | Proportion of native immobil. [% w/w] | Activity [U/g of immobilizate] (U/g of native immobil.) |
|---|---|---|---|---|---|
| TL01 on VPOC1600, native | 1 g | — | — | 100 | 261 |
| TL01 on VPOC1600, coated | 1 g | $a = 43, b = 5$ 250 μL | $a = 198$ 750 μL | 55 | 157 (285) |

Table 9 shows that the native preparation has an activity of 261 U/g, while the coated preparation has an activity of 157 U/g. Based on the content of native immobilizate, this represents an activity of 285 U/g; that is, a quantitative activity yield can be achieved within the margin of error.

Example 8

Production of an Esterase Preparation

Analogously to Example 7, an esterase from *R. oryzeae* is immobilized on Lewatit VPOC1600, coated and its activity determined in the hydrolysis of ethyl valerate.

TABLE 10

Activity determination of immobilized esterase from *R. oryzeae*.

| | Initial weight of native immobil. | Component of gen. formula I; c = d = 0; R1 = R2a = methyl, R2b = H | Component of gen. formula II; b = c = d = 0; R4 = methyl, R5 = vinyl | Proportion of native immobil. [% w/w] | Activity [U/g of immobilizate] (U/g of native immobil.) |
|---|---|---|---|---|---|
| Native VPOC1600 + esterase R.O. | 1 g | — | — | 100 | 67 |
| Coated VPOC1600 + E.R.O. | 1 g | a = 43, b = 5 250 μL | a = 198 750 μL | ca. 45 | 29.5 (65) |

Again, activity yield is quantitative within the margin of error.

Example 9

Production of a Laccase Preparation

Analogously to Example 4, a laccase (EC 1.10.3.2) from *Myceliophthora Theriophilia* (available as Flavorstar from Novozymes A/S) was immobilized on Lewatit VPOC 1600 (4.5 mg of protein on 1 g of Lewatit VPOC 1600), provided with a siloxane coating and tested for activity in ABTS assay.

TABLE 11

Activities of immobilized laccase

| Enzyme/ carrier | Initial weight of native immobil. | Component of gen. formula I; c = d = 0; R1 = R2a = methyl, R2b = H | Component of gen. formula II; b = c = d = 0; R4 = methyl, R5 = vinyl | Proportion of native immobil. [% w/w] | Activity [U/g of immob. (U/g of native immobil.)] | Activity U/g of protein | Relative Activity [%] |
|---|---|---|---|---|---|---|---|
| Laccase/ VPOC1600 native | 1 g | — | — | 100 | 0.41 | 91 | 100 |
| Laccase/ VPOC1600 coated | 1 g | a = 43, b = 5 250 μL | a = 98 750 μL | 33 | 0.022 (0.066) | 14.6 | 16 |

Table 11 shows that laccases can also be coated using the method of the present invention.

Having thus described in detail various embodiments of the present invention, it is to be understood that many apparent variations thereof are possible without departing from the spirit or scope of the present invention.

The invention claimed is:

1. An enzyme immobilizate which comprises one or more enzymes or microorganisms containing one or more enzymes which is immobilized on an inert carrier particle which is coated with a silicone obtained by hydrosilylation.

2. The enzyme immobilizate of claim 1 wherein the enzyme is a hydrolase.

3. The enzyme immobilizate of claim 2 wherein the inert carriers have a particle size distribution wherein at least 90% of the particles have a particle size of 10 to 5000 μm.

4. The enzyme immobilizate of claim 3 wherein the inert carriers are comprised of polyvinylstyrene, polymethylacrylate or polyacrylate.

5. The enzyme immobilizate of claim 4 wherein the silicone coating is obtained by hydrosilylating SiH-functional polysiloxanes with polysiloxanes containing one or more terminal carbon-carbon double bond.

6. The enzyme immobilizate of claim 5 wherein the SiH-functional polysiloxanes are polysiloxanes for formula (I):

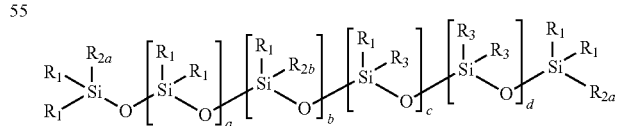

where
$N = a+b+c+d+2 = 3$ to $850$,
$a = 1$ to $800$,
$b = 0$ to $400$,
$c = 0$ to $10$,
$d = 0$ to $10$, $R_1$ are independently the same or different, and are selected from the group comprising: saturated or unsaturated, optionally branched alkyl groups having 1 to 30 carbon atoms, alkaryl radicals having 7 to 30 carbon atoms, aryl radicals having 6 to 30 carbon atoms;

$R_{2a}$ are independently hydrogen or $R_1$;

$R_{2b}$ are independently hydrogen or $R_1$;

$R_3$ are independently identical or different radicals of the general formula Ia:

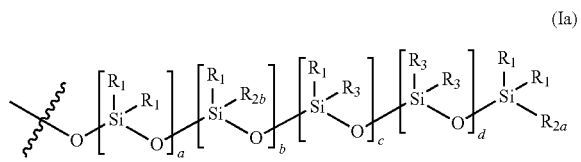
(Ia)

where $N=a+b+c+d+2=3$ to 850, preferably 6 to 160, a=1 to 800, b=0 to 400, c=0 to 10, d=0 to 10, $R_1$ are independently the same or different, and are selected from the group comprising: saturated or unsaturated, optionally branched alkyl groups having 1 to 30 carbon atoms, alkaryl radicals having 7 to 30 carbon atoms, aryl radicals having 6 to 30 carbon atoms;

$R_{2a}$ are independently hydrogen or $R_1$;

$R_{2b}$ are independently hydrogen or $R_1$;

$R_3$ are independently identical or different radicals of the formula Ia or an $R_1$ radical.

7. The enzyme immobilizate of claim 6 wherein the SiH-functional polysiloxanes are polysiloxanes for formula (I):

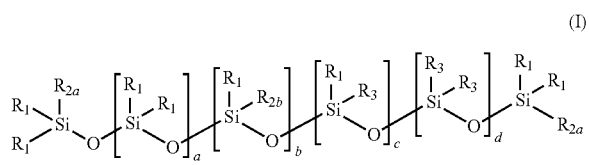
(I)

where $N=a+b+c+d+2=6$ to 160, a=2 to 150, b=2 to 75, c=0, d=0, $R_1$ are independently the same or different, and are selected from the group comprising: saturated or unsaturated, optionally branched alkyl groups having 1 to 30 carbon atoms, alkaryl radicals having 7 to 30 carbon atoms, aryl radicals having 6 to 30 carbon atoms;

$R_{2a}$ are independently hydrogen or $R_1$;

$R_{2b}$ are independently hydrogen or $R_1$.

8. The enzyme immobilizate of claim 7 wherein the polysiloxanes containing a terminal carbon-carbon double bond are polysiloxanes for formula (II):

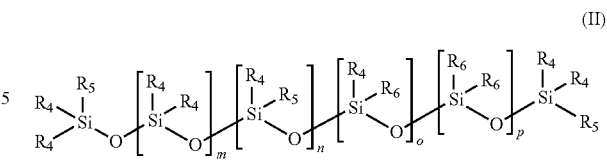
(II)

where $N=m+n+o+p+2=3$ to 1000, m=1 to 800, n=0 to 20, o=0 to 10, p=0 to 10, $R_4$ are independently the same or different and are from the following group: saturated or unsaturated, optionally branched alkyl groups having 1 to 30 carbon atoms, alkaryl radicals having 7 to 30 carbon atoms, aryl radicals having 6 to 30 carbon atoms;

$R_5$ are independently a terminally unsaturated alkyl or alkoxy radical or $R_4$;

$R_6$ are independently identical or different radicals of the general formula IIa:

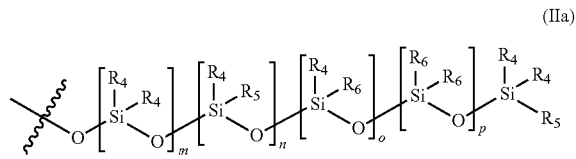
(IIa)

where $N=m+n+o+p+2=3$ to 1000, m=1 to 800, n=0 to 20, o=0 to 10, p=0 to 10, $R_4$ are independently the same or different and are from the following group: saturated or unsaturated, optionally branched alkyl groups having 1 to 30 carbon atoms, alkaryl radicals having 7 to 30 carbon atoms, aryl radicals having 6 to 30 carbon atoms;

$R_5$ are independently a terminally unsaturated alkyl or alkoxy radical, or $R_4$;

$R_6$ are independently identical or different radicals of the general formula IIa or $R_4$ radicals.

9. The enzyme immobilizate of claim 8 wherein the polysiloxanes containing a terminal carbon-carbon double bond are polysiloxanes for formula (II):

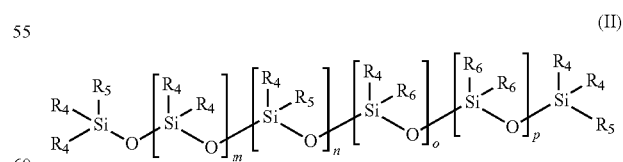
(II)

where $N=m+n+o+p+2=10$ to 600, m=2 to 600, n=0 to 10, o=0, p=0, $R_4$ are independently the same or different and are from the following group: saturated or unsaturated, optionally branched alkyl groups having 1 to 30 carbon atoms, alkaryl radicals having 7 to 30 carbon atoms, aryl radicals having 6 to 30 carbon atoms;

$R_5$ are independently a terminally unsaturated alkyl or alkoxy radical.

10. A process for preparing enzyme immobilizate according to claim 1, which comprises immobilizing the enzyme(s) or microorganisms containing enzyme(s) on an inert carrier and subsequently coating the enzyme containing inert carrier with a siloxane obtained by hydrosilylation.

11. The process of claim 10, wherein the siloxane coating is formed by contacting the enzyme containing inert carrier with a reaction mixture which comprises SiH-functional polysiloxanes, polysiloxanes containing terminal carbon-carbon double bonds and a catalyst which catalyzes the hydrosilylation under hydrosilylation conditions.

12. The enzyme immobilizate of claim 1 wherein the hydrolase is a lipase.

* * * * *